United States Patent
Toda

(10) Patent No.: US 11,903,604 B2
(45) Date of Patent: Feb. 20, 2024

(54) ULTRASOUND TRANSDUCER AND TREATMENT TOOL THAT INCLUDES A PIEZOELECTRIC ELEMENT AND A HORN

(71) Applicant: OLYMPUS CORPORATION, Hachioji (JP)

(72) Inventor: Masaya Toda, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 537 days.

(21) Appl. No.: 17/179,035

(22) Filed: Feb. 18, 2021

(65) Prior Publication Data
US 2022/0257278 A1 Aug. 18, 2022

(51) Int. Cl.
*A61B 17/32* (2006.01)
*B06B 3/00* (2006.01)

(52) U.S. Cl.
CPC ........ *A61B 17/320068* (2013.01); *B06B 3/00* (2013.01); *A61B 2017/320089* (2017.08)

(58) Field of Classification Search
CPC ........... A61B 17/320068; A61B 2017/320089; B06B 3/00
See application file for complete search history.

(56) References Cited

U.S. PATENT DOCUMENTS

| 2019/0223900 A1 | 7/2019 | Toda |
| 2020/0214737 A1* | 7/2020 | Ian ..................... A61B 10/0233 |
| 2021/0177453 A1* | 6/2021 | Akagane ............... B06B 1/0611 |

FOREIGN PATENT DOCUMENTS

JP 6234641 B1 11/2017

* cited by examiner

*Primary Examiner* — Emily P Pham
(74) *Attorney, Agent, or Firm* — Oliff PLC

(57) ABSTRACT

An ultrasound transducer includes: a piezoelectric element unit including a plurality of piezoelectric elements configured to generate an ultrasound vibration; and a horn that extends from a distal end toward a proximal end to define a longitudinal axis direction and that is connected to a distal end side of the piezoelectric element unit. The horn includes a first transformation portion whose cross-sectional area orthogonal to the longitudinal axis direction decreases toward a distal end, the first transformation portion being configured to amplify amplitude of the ultrasound vibration, and a second transformation portion that is provided between the first transformation portion and a connection position at which the horn and the piezoelectric element unit are connected, the second transformation portion being configured to amplify or attenuates the amplitude of the ultrasound vibration.

12 Claims, 3 Drawing Sheets

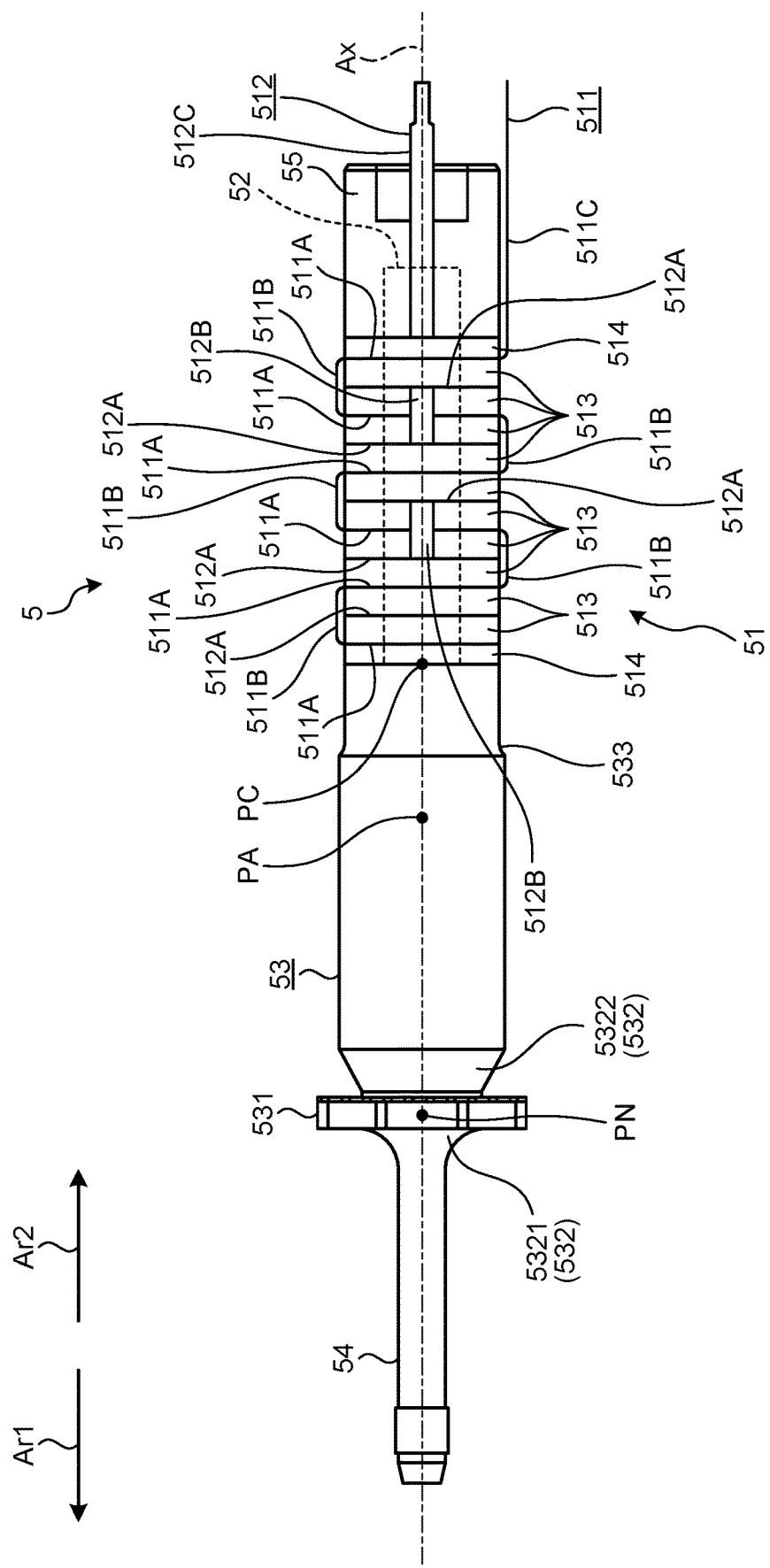

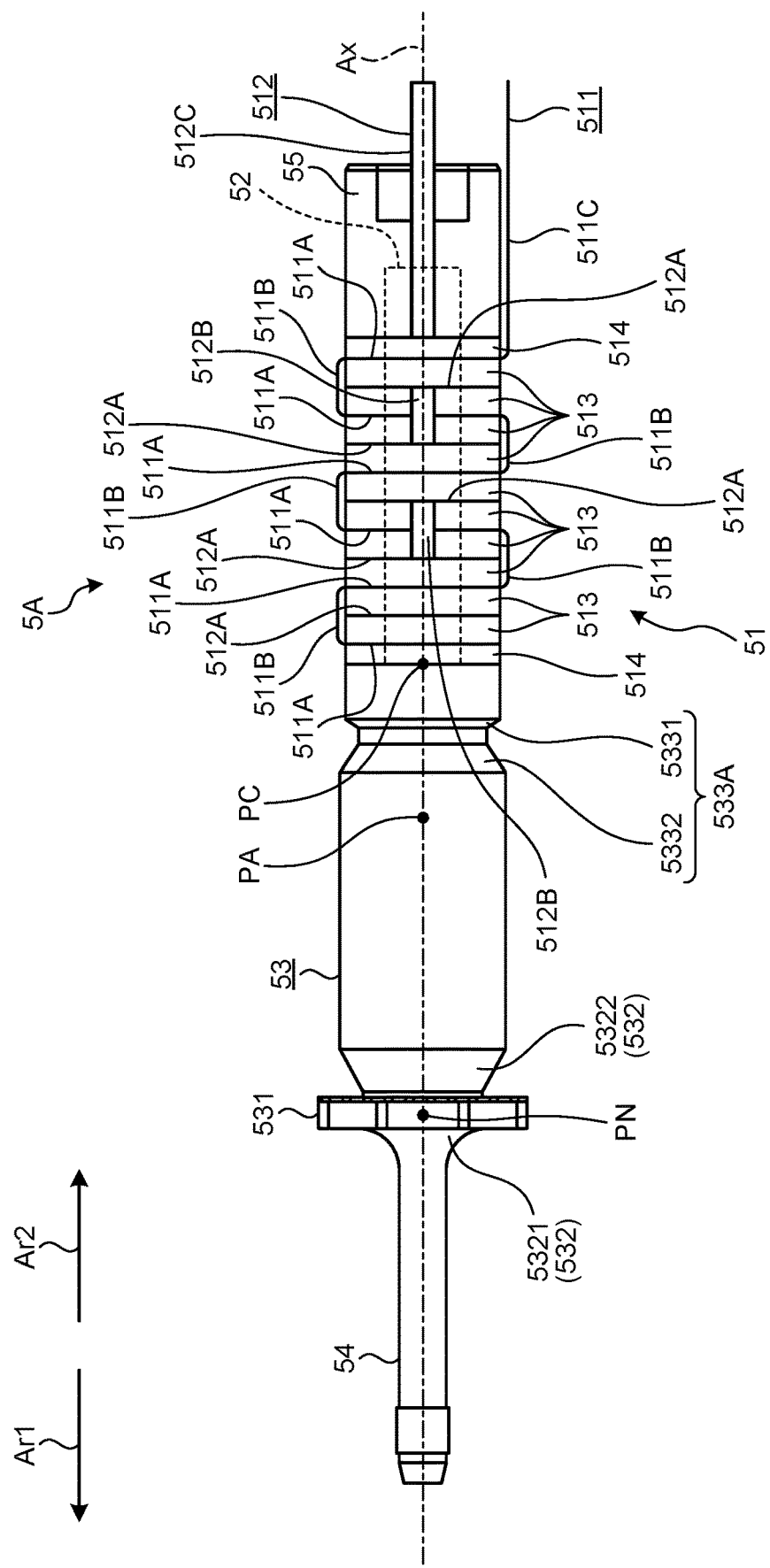

ULTRASOUND TRANSDUCER AND TREATMENT TOOL THAT INCLUDES A PIEZOELECTRIC ELEMENT AND A HORN

BACKGROUND

1. Technical Field

The present disclosure relates to an ultrasound transducer and a treatment tool.

2. Related Art

In the related art, a treatment tool that applies an ultrasound vibration to a region to be treated (hereinafter, referred to as target region) in a living tissue and treats the target region has been known (see, for example, Japanese Patent No. 6234641, hereinafter, referred to as Patent Literature 1).

In the treatment tool described in Patent Literature 1, a bolt-clamped Langevin type transducer (BLT) in which a plurality of piezoelectric elements is laminated is employed as an ultrasound transducer that generates an ultrasound vibration.

SUMMARY

In some embodiments, an ultrasound transducer includes: a piezoelectric element unit including a plurality of piezoelectric elements configured to generate an ultrasound vibration; and a horn that extends from a distal end toward a proximal end to define a longitudinal axis direction and that is connected to a distal end side of the piezoelectric element unit, the horn including a first transformation portion whose cross-sectional area orthogonal to the longitudinal axis direction decreases toward a distal end, the first transformation portion being configured to amplify amplitude of the ultrasound vibration, and a second transformation portion that is provided between the first transformation portion and a connection position at which the horn and the piezoelectric element unit are connected, the second transformation portion being configured to amplify or attenuates the amplitude of the ultrasound vibration.

In some embodiments, a treatment tool includes: an ultrasound transducer configured to generate an ultrasound vibration; and a vibration transmission member that is connected to the ultrasound transducer, the vibration transmission member being configured to transmit the ultrasound vibration. The ultrasound transducer includes a piezoelectric element unit including a plurality of piezoelectric elements configured to generate the ultrasound vibration, and a horn that extends from a distal end toward a proximal end to define a longitudinal axis direction and that is connected to a distal end side of the piezoelectric element unit, the horn including a first transformation portion whose cross-sectional area orthogonal to the longitudinal axis direction decreases toward a distal end, the first transformation portion being configured to amplify amplitude of the ultrasound vibration, and a second transformation portion that is provided between the first transformation portion and a connection position at which the horn and the piezoelectric element unit are connected, the second transformation portion being configured to amplify or attenuates the amplitude of the ultrasound vibration.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 2 is a view illustrating an ultrasound transducer; and

FIG. 3 is a view illustrating an ultrasound transducer according to another exemplary embodiment.

DETAILED DESCRIPTION

Figure 1:
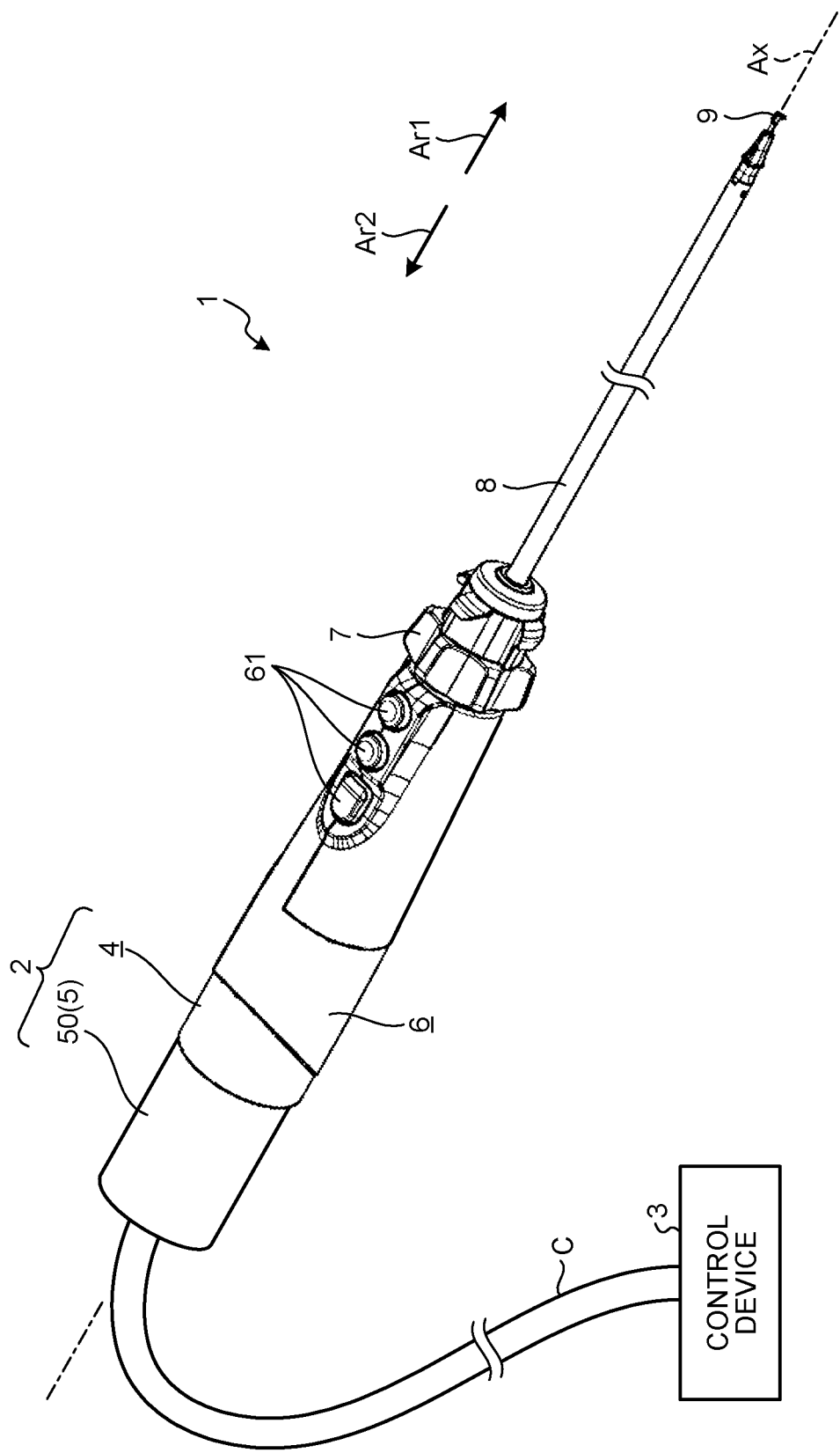
FIG. 1 is a view illustrating a treatment system according to an exemplary embodiment.

In the following, modes for carrying out the present disclosure (hereinafter, referred to as "embodiment") will be described with reference to the drawings. Note that the present disclosure is not limited to the embodiments described in the following. Furthermore, the same reference sign is assigned to identical parts in the drawings.

First Embodiment

Schematic Configuration of Treatment System

FIG. 1 is a view illustrating a treatment system 1 according to an exemplary embodiment.

By applying treatment energy to a region to be treated (hereinafter, referred to as target region) in a living tissue, a treatment system 1 treats the target region. In the present embodiment, ultrasound energy and high-frequency energy are employed as the treatment energy. Also, examples of the treatment include coagulation and incision of the target region. As illustrated in FIG. 1, this treatment system 1 includes a treatment tool 2 and a control device 3.

Configuration of Treatment Tool

The treatment tool 2 is an ultrasound treatment tool that treats a target region by at least applying ultrasound energy to the target region. As illustrated in FIG. 1, this treatment tool 2 includes a treatment tool main body 4 and an ultrasound transducer 5.

The treatment tool main body 4 is a portion that applies treatment energy to the target region. As illustrated in FIG. 1, this treatment tool main body 4 includes a housing 6, a rotary knob 7, a sheath 8, and a vibration transmission member 9.

Note that one side along a central axis Ax of the sheath 8 will be referred to as a distal end side Ar1, and the other side will be referred to as a proximal end side Ar2 in the following. The central axis Ax corresponds to a longitudinal axis according to the present disclosure.

The housing 6 has a substantially cylindrical shape coaxial with the central axis Ax. Then, the housing 6 supports the entire treatment tool main body 4.

As illustrated in FIG. 1, switches 61 that are provided in a state of being exposed to the outside and that receive treatment start operation by an operator are provided in this housing 6. The switches 61 output an operation signal corresponding to the treatment start operation to the control device 3 through an electric cable C (FIG. 1) that electrically connects the treatment tool 2 and the control device 3.

As illustrated in FIG. 1, the rotary knob 7 has a substantially cylindrical shape coaxial with the central axis Ax, and is provided on the distal end side Ar1 of the housing 6. This rotary knob 7 receives rotational operation by the operator. The rotational operation is operation of rotating the vibration transmission member 9 around the central axis Ax. Then, the rotary knob 7, the sheath 8, and the vibration transmission member 9 rotate around the central axis Ax by the rotational operation.

The sheath 8 is a cylindrical pipe made of a material such as metal, and an end portion thereof on the proximal end side Ar2 is supported by the housing 6. Then, the vibration transmission member 9 is inserted into the sheath 8.

The vibration transmission member 9 is made of an electrically conductive material and has an elongated shape extending along the central axis Ax. Also, the vibration transmission member 9 is inserted into the sheath 8 in a state in which an end portion on the distal end side Ar1 is exposed to the outside. Furthermore, a proximal end of the vibration transmission member 9 is connected to the ultrasound transducer 5. Then, the vibration transmission member 9 transmits an ultrasound vibration generated by the ultrasound transducer 5 from the end portion on the proximal end side Ar2 to the end portion on the distal end side Ar1. In the present embodiment, the ultrasound vibration is a longitudinal vibration that vibrates in a direction along the central axis Ax.

The ultrasound transducer 5 includes a bolt-clamped Langevin type transducer (BLT) that generates an ultrasound vibration in response to supply of a drive signal that is AC power. This ultrasound transducer 5 is inserted into the housing 6 from the proximal end side Ar2 of the housing 6 in a state of being housed in a transducer (TD) case 50, and is detachably connected to the housing 6.

Note that a detailed configuration of the ultrasound transducer 5 will be described in "Configuration of ultrasound transducer" described later.

Configuration of Control Device

The treatment tool 2 is detachably connected to the control device 3 by the electric cable C. Then, the control device 3 comprehensively controls an operation of the treatment tool 2 as described below in response to the operation signal (treatment start operation) input from the switches 61 through the electric cable C.

The control device 3 outputs a drive signal to the ultrasound transducer 5 through the electric cable C. As a result, the ultrasound transducer 5 generates an ultrasound vibration (longitudinal vibration). Also, the vibration transmission member 9 vibrates with desired amplitude due to the longitudinal vibration. Then, to a target region in contact with an end portion on the distal end side Ar1 of the vibration transmission member 9, an ultrasound vibration is applied from the end portion on the distal end side Ar1. In other words, ultrasound energy is applied to the target region from the end portion on the distal end side Ar1.

Also, the control device 3 is connected to a return electrode (not illustrated) by an electric cable (not illustrated). The return electrode is attached to a surface of a subject. Furthermore, the control device 3 is electrically connected to the vibration transmission member 9 through the electric cable C, and through a fastening portion 55, an element mounting portion 52, a horn 53, and a probe mounting portion 54 that are described later. Then, the control device 3 outputs a high-frequency signal, which is high-frequency power, between the vibration transmission member 9 and the return electrode plate through the electric cable, the electric cable C, the fastening portion 55, the element mounting portion 52, the horn 53, and the probe mounting portion 54. As a result, a high-frequency current flows in the target region placed between the end portion on the distal end side Ar1 of the vibration transmission member 9 and the return electrode plate. In other words, high-frequency energy is applied to the target region from the end portion on the distal end side Ar1.

Configuration of Ultrasound Transducer

Next, a configuration of the above-described ultrasound transducer 5 will be described.

FIG. 2 is a view illustrating the ultrasound transducer 5.

As illustrated in FIG. 2, the ultrasound transducer 5 includes a piezoelectric element unit 51, an element mounting portion 52, a horn 53, a probe mounting portion 54, and a fastening portion 55.

As illustrated in FIG. 2, the piezoelectric element unit 51 includes first and second electrode plates 511 and 512, a plurality of (ten in the present embodiment) piezoelectric elements 513, and two insulating plates 514 having an electrical insulation property.

The first and second electrode plates 511 and 512 are portions to which a drive signal is supplied from the control device 3.

As illustrated in FIG. 2, the first electrode plate 511 includes a plurality of (six in the present embodiment) negative electrode plates 511A, a plurality of (five in the present embodiment) negative electrode wiring portions 511B, and a negative electrode terminal 511C.

The plurality of negative electrode plates 511A is provided side by side along the central axis Ax, each having a disk shape with an opening (not illustrated) at a center.

The plurality of negative electrode wiring portions 511B is portions to electrically connect outer edge portions of negative electrode plates 511A adjacent to each other.

The negative electrode terminal 511C extends toward the proximal end side Ar2 from an outer edge of a negative electrode plate 511A placed on the most proximal end side Ar2 among the plurality of negative electrode plates 511A. Then, the negative electrode terminal 511C is electrically connected to the control device 3 through the electric cable C.

As illustrated in FIG. 2, the second electrode plate 512 includes a plurality of (five in the present embodiment) positive electrode plates 512A, positive electrode wiring portions 512B (four portions in the present embodiment), and a positive electrode terminal 512C.

The plurality of positive electrode plates 512A is provided side by side along the central axis Ax, each having a disk shape with an opening (not illustrated) at a center. Note that the positive electrode plates 512A have substantially the same shape as the negative electrode plates 511A.

Then, the negative electrode plates 511A and the positive electrode plates 512A are alternately arranged along the central axis Ax as illustrated in FIG. 2. At this time, the negative electrode plate 511A placed on the most proximal end side Ar2 among the plurality of negative electrode plates 511A is arranged in a position close to the fastening portion 55 compared to a positive electrode plate 512A placed on the most proximal end side Ar2 among the plurality of positive electrode plates 512A.

The positive electrode wiring portions 512B are portions to electrically connect outer edge portions of positive electrode plates 512A adjacent to each other.

The positive electrode terminal 512C extends toward the proximal end side Ar2 from an outer edge of the positive electrode plate 512A placed on the most proximal end side Ar2 among the plurality of positive electrode plates 512A. Then, the positive electrode terminal 512C is electrically connected to the control device 3 through the electric cable C. Then, from the control device 3, a drive signal is supplied between the negative electrode terminal 511C and the positive electrode terminal 512C.

The plurality of piezoelectric elements 513 is respectively arranged between the negative electrode plates 511A and the positive electrode plates 512A, each having a disk shape with an opening (not illustrated) at a center. That is, the plurality of piezoelectric elements 513 is laminated along the central axis Ax. Then, since a potential difference is generated in a lamination direction along the central axis Ax in response to a drive signal supplied to the first and second electrode plates 511 and 512, the plurality of piezoelectric elements 513 repeats expansion and contraction alternately in the lamination direction. As a result, the piezoelectric element unit 51 generates an ultrasound vibration of a longitudinal vibration in which the lamination direction is a vibration direction.

The element mounting portion 52, the horn 53, and the probe mounting portion 54 are members integrally formed of an electrically conductive material.

The element mounting portion 52 is a bolt extending linearly along the central axis Ax, and is inserted into each of the openings (not illustrated) in the plurality of negative electrode plates 511A, each of the openings (not illustrated) in the plurality of positive electrode plates 512A, and each of the openings (not illustrated) in the plurality of piezoelectric elements 513. Then, as illustrated in FIG. 2, the fastening portion 55 that is a nut made of an electrically conductive material is attached to an end portion on the proximal end side Ar2 of the element mounting portion 52.

The horn 53 is provided at an end portion on the distal end side Ar1 of the element mounting portion 52, and has a substantially columnar shape extending linearly along the central axis Ax. That is, the horn 53 is connected to the distal end side Ar1 of the piezoelectric element unit 51. Also, as illustrated in FIG. 2, an end portion on the proximal end side Ar2 of the horn 53 is set to have a larger diameter size than the element mounting portion 52. That is, the plurality of negative electrode plates 511A, the plurality of positive electrode plates 512A, and the plurality of piezoelectric elements 513 are integrally fastened in a state of having a substantially columnar shape by being sandwiched between the horn 53 and the fastening portion 55 in a state in which the element mounting portion 52 penetrates along the central axis Ax. Note that the insulating plates 514 are respectively arranged between the horn 53 and a negative electrode plate 511A placed on the most distal end side Ar1 among the plurality of negative electrode plates 511A, and between the fastening portion 55 and the negative electrode plate 511A placed on the most proximal end side Ar2 among the plurality of negative electrode plates 511A.

Note that a detailed configuration of the horn 53 will be described in "Configuration of horn" described later.

As illustrated in FIG. 2, the probe mounting portion 54 is provided at an end portion on the distal end side Ar1 of the horn 53, and extends linearly along the central axis Ax. Then, an end portion on the distal end side Ar1 of the probe mounting portion 54 is mechanically and electrically connected to the end portion on the proximal end side Ar2 of the vibration transmission member 9 when the TD case 50 in which the ultrasound transducer 5 is housed is connected to the housing 6.

Configuration of Horn

Next, a configuration of the above-described horn 53 will be described.

As illustrated in FIG. 2, the horn 53 includes a flange portion 531, a first transformation portion 532, and a second transformation portion 533.

The flange portion 531 is a portion that has the largest diameter size in the horn 53 and that is used to support the ultrasound transducer 5 with respect to the TD case 50. This flange portion 531 is provided in a node position PN (FIG. 2) of an ultrasound vibration generated by the ultrasound transducer 5.

As illustrated in FIG. 2, the first transformation portion 532 includes a distal end-side transformation portion 5321 continuously provided on the distal end side Ar1 with respect to the flange portion 531 (node position PN) and a proximal end-side transformation portion 5322 continuously provided on the proximal end side Ar2 with respect to the flange portion 531 (node position PN).

Each of these distal end-side transformation portion 5321 and proximal end-side transformation portion 5322 has a truncated cone shape in which a cross-sectional area orthogonal to the central axis Ax decreases toward the distal end side Ar1. That is, with the shape, the distal end-side transformation portion 5321 and the proximal end-side transformation portion 5322 provided in the vicinity of the node position PN have a function of expanding amplitude of an ultrasound vibration. In other words, the distal end-side transformation portion 5321 and the proximal end-side transformation portion 5322 have a function of increasing a transformation ratio (magnification rate of amplitude of an ultrasound vibration) in the horn 53. Note that the distal end-side transformation portion 5321 and the proximal end-side transformation portion 5322 do not necessarily have the truncated cone shape, and may be configured by a so-called stepped horn in which a cross-sectional area orthogonal to a central axis Ax changes in a stepped manner along the central axis Ax.

Incidentally, it is known that a transformation ratio is generated in a boundary position of different materials since physical properties (specifically, Young's modulus) are different. For example, a connection position PC (FIG. 2) in which the horn 53 and the piezoelectric element unit 51 are connected corresponds to the boundary position. Also, due to a manufacturing error in the piezoelectric elements 513, there is a case where Young's modulus of the plurality of piezoelectric elements 513 as a whole becomes smaller than design Young's modulus. In such a case, a transformation ratio in the connection position PC becomes larger than a design transformation ratio. Then, the second transformation portion 533 according to the present embodiment has a function of canceling the transformation ratio increased due to the manufacturing error in the piezoelectric elements 513.

Specifically, the second transformation portion 533 is provided between the connection position PC at which the horn 53 and the piezoelectric element unit 51 are connected, and the first transformation portion 532. More specifically, the second transformation portion 533 is provided between an antinode position PA of an ultrasound vibration, which position is placed on the most proximal end side Ar2 between the connection position PC and the first transformation portion 532, and the connection position PC. Here, the second transformation portion 533 is placed in a position of 0.1λ from the antinode position PA in a case where a wavelength of the ultrasound vibration is λ. That is, the second transformation portion 533 is provided in the vicinity of the antinode position PA. Note that in the present embodiment, only one antinode position PA of an ultrasound vibration is provided between the connection position PC and the first transformation portion 532. However, a plurality of antinode positions PA may be provided.

Also, the second transformation portion 533 has a shape in which a cross-sectional area orthogonal to the central axis Ax changes along the central axis Ax. In the present embodiment, the second transformation portion 533 includes a truncated cone-shaped cross-sectional area increasing portion in which the cross-sectional area orthogonal to the central axis Ax increases toward the distal end side Ar1. That is, with the shape, the second transformation portion 533 has a function of attenuating amplitude of the ultrasound vibration and canceling a transformation ratio increased due to the manufacturing error in the piezoelectric elements 513 described above. Here, in the second transformation portion 533, a diameter after an increase in the cross-sectional area is set to be smaller than a size of a diameter before the increase in the cross-sectional area×1.1. Specifically, it is desirable that the diameter after the increase in the cross-sectional area is set to a size of the diameter before the increase in the cross-sectional area×1.02 to 1.09, preferably set to a size of the diameter before the increase in the cross-sectional area×1.05 to 1.07, and more preferably set to a size of the diameter before the increase in the cross-sectional area×1.06. Note that the second transformation portion 533 does not necessarily have the truncated cone shape, and may be configured by a so-called stepped horn in which a cross-sectional area orthogonal to a central axis Ax changes in a stepped manner along the central axis Ax.

Also, a diameter of the horn 53 in the connection position PC is larger than a diameter of the piezoelectric element unit 51 in the connection position PC (diameter of insulating plate 514 (piezoelectric element 513)). More specifically, the diameter of the horn 53 in the connection position PC is set to a size of the diameter of the piezoelectric element unit 51 in the connection position PC×1.00 to 1.07. The diameter of the horn 53 in the connection position PC is preferably set to a size of the diameter of the piezoelectric element unit 51×1.01 to 1.06, and is more preferably set to a size of the diameter of the piezoelectric element unit 51×1.03. Note that similarly to the second transformation portion 533, the connection position PC having the diameter size relationship has a function of attenuating amplitude of the ultrasound vibration and canceling a transformation ratio increased due to a manufacturing error in the piezoelectric elements 513 described above.

Note that a diameter from the connection position PC to the second transformation portion 533 (before an increase in the cross-sectional area) is the same in the horn 53. Also, a diameter from the second transformation portion 533 (after the increase in the cross-sectional area) to the proximal end-side transformation portion 5322 (before a decrease in the cross-sectional area) is the same in the horn 53.

According to the present embodiment described above, the following effects are acquired.

In the ultrasound transducer 5 according to the present embodiment, the above-described second transformation portion 533 is provided in the horn 53. Also, in the connection position PC, a diameter of the horn 53 and a diameter of the piezoelectric element unit 51 are set in the above-described relationship. Thus, a transformation ratio increased due to a manufacturing error in the piezoelectric elements 513 described above can be canceled by the second transformation portion 533 and the connection position PC, and amplitude of an ultrasound vibration can be set to desired amplitude.

Next, another exemplary embodiment will be described.

In the following description, the same reference sign is assigned to a configuration similar to that of the first embodiment described above, and a detailed description thereof will be omitted or simplified.

FIG. 3 is a view illustrating an ultrasound transducer 5A according to the present embodiment.

As illustrated in FIG. 3, in the ultrasound transducer 5A according to the present embodiment, a second transformation portion 533A having a shape different from that of the second transformation portion 533 is employed with respect to the ultrasound transducer 5 described in the first embodiment described above.

Incidentally, due to a manufacturing error in piezoelectric elements 513, there is a case where Young's modulus of a plurality of piezoelectric elements 513 as a whole becomes larger than design Young's modulus. In such a case, a transformation ratio in a connection position PC becomes smaller than a design transformation ratio. Then, the second transformation portion 533A according to the present embodiment has a function of canceling the transformation ratio decreased due to the manufacturing error in the piezoelectric elements 513.

Specifically, in a horn 53, the second transformation portion 533A is provided in the same position as the second transformation portion 533 described in the first embodiment described above. That is, the second transformation portion 533A is provided in the vicinity of an antinode position PA.

Also, the second transformation portion 533A has a shape in which a cross-sectional area orthogonal to a central axis Ax changes along the central axis Ax. Specifically, as illustrated in FIG. 3, the second transformation portion 533A includes a cross-sectional area decreasing portion 5331 and a cross-sectional area increasing portion 5332.

The cross-sectional area decreasing portion 5331 has a truncated cone shape in which a cross-sectional area orthogonal to the central axis Ax decreases toward a distal end side Ar1. That is, with the shape, the cross-sectional area decreasing portion 5331 has a function of amplifying amplitude of an ultrasound vibration and canceling a transformation ratio decreased due to a manufacturing error in the piezoelectric elements 513 described above. Here, a diameter after the decrease in the cross-sectional area in the cross-sectional area decreasing portion 5331 is set to a size of a diameter before the decrease in the cross-sectional area×0.85 to 0.91. The diameter after the decrease in the cross-sectional area in the cross-sectional area decreasing portion 5331 is preferably set to a size of the diameter before the decrease in the cross-sectional area×0.87 to 0.89, and is more preferably set to a size of the diameter before the decrease in the cross-sectional area×0.88. Note that the cross-sectional area decreasing portion 5331 does not necessarily have the truncated cone shape, and may be configured by a so-called stepped horn in which a cross-sectional area orthogonal to a central axis Ax changes in a stepped manner along the central axis Ax.

The cross-sectional area increasing portion 5332 is continuously provided on the distal end side Ar1 of the cross-sectional area decreasing portion 5331. This cross-sectional area increasing portion 5332 has a truncated cone shape in which a cross-sectional area orthogonal to the central axis Ax increases toward the distal end side Ar1. Note that since the cross-sectional area increasing portion 5332 is provided in a position close to the antinode position PA, a function of decreasing amplitude of an ultrasound vibration with the shape is weak. Since this cross-sectional area increasing portion 5332 is provided, a diameter before the decrease in the cross-sectional area in a proximal end-side transformation portion 5322 can be increased. Thus, a function of increasing a transformation ratio in the proximal end-side transformation portion 5322 becomes sufficient. Here, a diameter after an increase in the cross-sectional area in the cross-sectional area increasing portion 5332 is set to a size around the diameter before the decrease in the cross-sectional area in the cross-sectional area decreasing portion 5331×1.10 to 1.4. The diameter of the cross-sectional area increasing portion 5332 after the increase in the cross-sectional area is preferably set to a size of the diameter before the decrease in the cross-sectional area×1.23 to 1.25, and is more preferably set to a size of the diameter before the decrease in the cross-sectional area×1.24. Note that in FIG. 3, a size along the central axis Ax in the cross-sectional area decreasing portion 5331 is illustrated smaller than a size along the central axis Ax in the cross-sectional area increasing portion 5332. However, this is not a limitation. For example, a size along a central axis Ax in a cross-sectional area decreasing portion 5331 may be larger than or the same as a size along the central axis Ax in a cross-sectional area increasing portion 5332. Note that the cross-sectional area increasing portion 5332 does not necessarily have the truncated cone shape, and may be configured by a so-called stepped horn in which a cross-sectional area orthogonal to a central axis Ax changes in a stepped manner along the central axis Ax.

Even in a case where the second transformation portion 533A of the present embodiment described above is employed, effects similar to those of the first embodiment described above are acquired.

Other Embodiments

Although modes for carrying out the present disclosure have been described above, the present disclosure is not limited only to the above-described embodiments.

In the treatment tool 2 according to the above-described embodiments, a configuration of applying each of ultrasound energy and high-frequency energy to a target region is employed. However, this is not a limitation, and a configuration of applying only ultrasound energy to a target region may be employed. In this case, two insulating plates 514 can be omitted.

In the above-described embodiments, a treatment tool of performing treatment when an end portion on a distal end side Ar1 of a vibration transmission member 9 is made to come into contact with a target region is employed as a treatment tool according to the present disclosure. However, this is not a limitation. As a treatment tool according to the present disclosure, a treatment tool that performs treatment by gripping a target region between an end portion on a distal end side Ar1 of a vibration transmission member 9 and a jaw may be employed.

In each of the ultrasound transducers 5 and 5A according to the above-described embodiments, a second transformation portion according to the present disclosure is configured to have a shape in which a cross-sectional area orthogonal to a central axis Ax changes along the central axis Ax. However, this is not a limitation. For example, as a second transformation portion according to the present disclosure, a configuration in which different materials having different Young's moduli are connected may be employed.

In the second embodiment described above, a cross-sectional area increasing portion 5332 may not be provided and a second transformation portion 533A may only include a cross-sectional area decreasing portion 5331.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound transducer comprising:
    a piezoelectric element unit including a plurality of piezoelectric elements configured to generate an ultrasound vibration; and
    a horn that extends from a distal end toward a proximal end to define a longitudinal axis direction and that is connected to a distal end side of the piezoelectric element unit, the horn including:
        a first transformation portion whose cross-sectional area orthogonal to the longitudinal axis direction decreases toward a distal end, the first transformation portion being configured to amplify amplitude of the ultrasound vibration, and
        a second transformation portion that is provided between the first transformation portion and a connection position at which the horn and the piezoelectric element unit are connected, the second transformation portion being configured to change the amplitude of the ultrasound vibration.

2. The ultrasound transducer according to claim 1, wherein
    the second transformation portion is provided between the connection position and an antinode position of the ultrasound vibration, the antinode position being provided at a most proximal end side between the connection position and the first transformation portion.

3. The ultrasound transducer according to claim 2, wherein
    the second transformation portion has a cross-sectional area orthogonal to the longitudinal axis that changes along the longitudinal axis.

4. The ultrasound transducer according to claim 3, wherein
    the second transformation portion includes a cross-sectional area increasing portion that has a cross-sectional area orthogonal to the longitudinal axis that increases toward a distal end.

5. The ultrasound transducer according to claim 3, wherein
    the second transformation portion includes a cross-sectional area decreasing portion having cross-sectional area orthogonal to the longitudinal axis direction that decreases toward a distal end.

6. The ultrasound transducer according to claim 5, wherein
    the second transformation portion includes a cross-sectional area increasing portion provided on a distal end side of the cross-sectional area decreasing portion, the cross-sectional area increasing portion having a cross-sectional area orthogonal to the longitudinal axis direction that increases toward a distal end.

7. The ultrasound transducer according to claim 1, wherein:
    a diameter of the piezoelectric element unit at the connection position is smaller than a diameter of the horn at the connection position.

8. The ultrasound transducer of claim 1, wherein the second transformation portion is configured to amplify the amplitude of the ultrasound vibration.

9. The ultrasound transducer of claim 1, wherein the second transformation portion is configured to attenuate the amplitude of the ultrasound vibration.

10. A treatment tool comprising:
  an ultrasound transducer configured to generate an ultrasound vibration; and
  a vibration transmission member that is connected to the ultrasound transducer, the vibration transmission member being configured to transmit the ultrasound vibration, wherein
  the ultrasound transducer includes
  a piezoelectric element unit including a plurality of piezoelectric elements configured to generate the ultrasound vibration, and
  a horn that extends from a distal end toward a proximal end to define a longitudinal axis direction and that is connected to a distal end side of the piezoelectric element unit, the horn including:
    a first transformation portion having a cross-sectional area orthogonal to the longitudinal axis direction that decreases toward a distal end, the first transformation portion being configured to amplify amplitude of the ultrasound vibration, and
    a second transformation portion that is provided between the first transformation portion and a connection position at which the horn and the piezoelectric element unit are connected, the second transformation portion being configured to change the amplitude of the ultrasound vibration.

11. The treatment tool of claim 10, wherein the second transformation portion is configured to amplify the amplitude of the ultrasound vibration.

12. The treatment tool of claim 10, wherein the second transformation portion is configured to attenuate the amplitude of the ultrasound vibration.

* * * * *